United States Patent [19]

Fountoulakis et al.

[11] Patent Number: 5,426,038
[45] Date of Patent: Jun. 20, 1995

[54] PROCESS FOR PRODUCTION OF AN ANTIBIOTIC COMPOUND WITH *ZALERION ARBORICOLA*

[75] Inventors: Jimmy M. Fountoulakis, Westfield; Prakash S. Masurekar, Warren, both of N.J.; Louis Kaplan, New City, N.Y.

[73] Assignee: Merck & Co, Inc., Rahway, N.J.

[21] Appl. No.: 195,426

[22] Filed: Feb. 14, 1994

Related U.S. Application Data

[63] Continuation of Ser. No. 878,137, May 4, 1992, abandoned, which is a continuation of Ser. No. 492,024, Mar. 12, 1990, abandoned.

[51] Int. Cl.⁶ ............................................. C12P 21/00
[52] U.S. Cl. .................................. 435/71.3; 435/71.1; 435/911; 435/254.1
[58] Field of Search ...................... 435/71.1, 71.3, 119, 435/911, 254.1

[56] References Cited

U.S. PATENT DOCUMENTS 4,931,352  6/1990  Fromtling ........................... 435/71.3

OTHER PUBLICATIONS

D. A. Hopwood, "The Isolation of Mutants" Ch. VII, pp. 363–433, Methods in Microbiology, vol. 3A, Academic Press, 1970.
C. T. Calam, "Improvement of Microorganisms by Mutation, Hydridization & Selection" Ch. VII, pp. 435–549, Methods in Microbiology, vol. 3A, Academic Press, 1970.
R. E. Schwartz, et al., J. Antibiotics 42, 163–167 (1989).
C. F. Wichmann, et al., J. Antibiotics 42, 168–173 (1989).

*Primary Examiner*—Irene Marx
*Attorney, Agent, or Firm*—Elliott Korsen; Mark R. Daniel; Joseph F. DiPrima

[57] ABSTRACT

A process for producing an antibiotic compound which is normally a minor component in the cultivation of *Z. arboricola* to be the major product is described.

1 Claim, No Drawings

PROCESS FOR PRODUCTION OF AN ANTIBIOTIC COMPOUND WITH ZALERION ARBORICOLA

This is a continuation of application Ser. No. 07/878,137 filed May 4, 1992, now abandoned, which is a continuation of application Ser. No. 07/492,024 filed Mar. 12, 1990, now abandoned.

BACKGROUND OF THE INVENTION

1- [4,5-dihydroxy-$N^2$-(10,12-dimethyl-1-oxo-tetradecyl)-L-ornithine]-5-(3-hydroxy-L, glutamine-6-(3-hydroxy-L-proline]echinocandin B having the formula

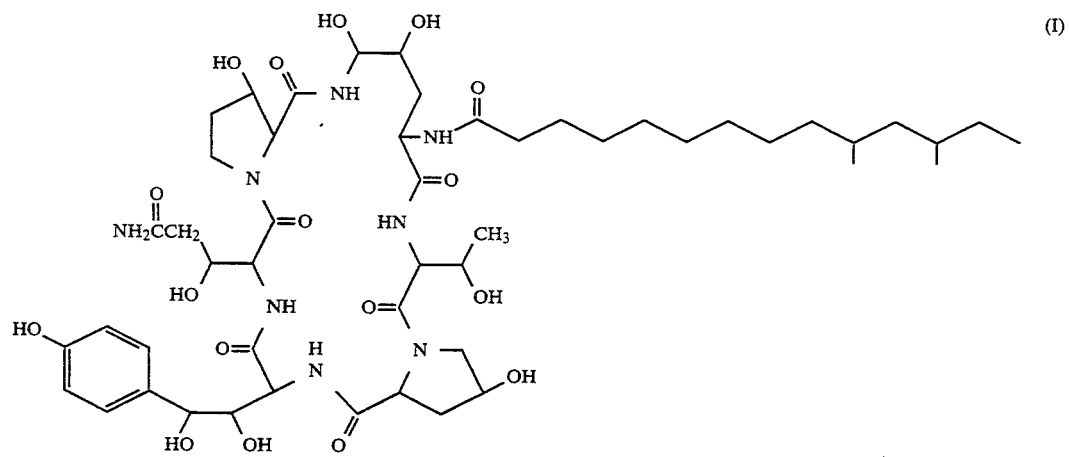

(hereinafter Compound I) and useful as an antibiotic agent as described and claimed in application Ser. No. 374,416, filed Jun. 30, 1989 now abandoned, and in application Ser. No. 492,025, filed Mar. 12. 1990, now abandoned, is normally produced as one of the minor components on the cultivation of MF 5171 *Zalerion arboricola* ATCC 20868. By use of various media and/or other modifications, it has been possible to improve the actual yield of Compound I; nevertheless, it has heretofore not been possible to produce it in an amount to exceed Compound X of the following structure:

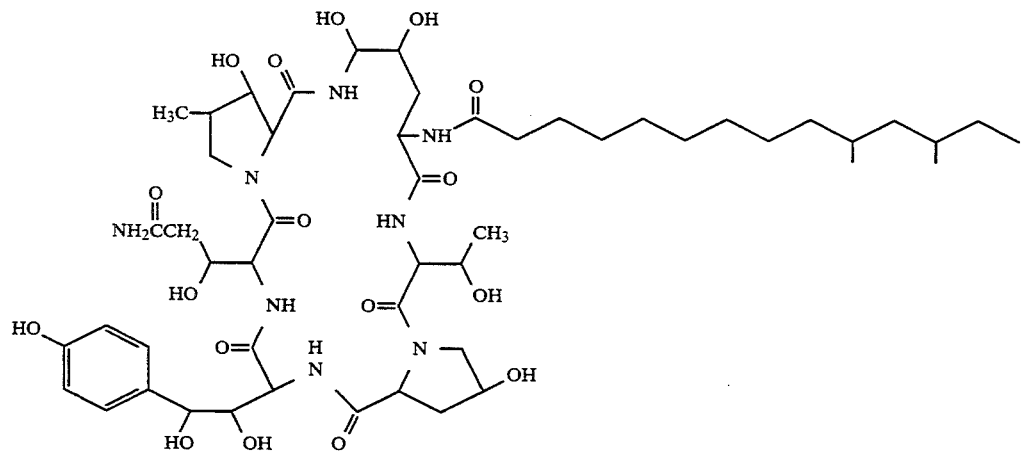

Compound X is described and claimed in application Ser. No. 362,647, filed Jun. 7, 1989 which is a continuation of Ser. No. 105,795 filed Oct. 7, 1987, now abandoned. It is desirable to find a way in which Compound I can be produced as the major component.

DESCRIPTION OF THE INVENTION

According to the present invention there has been discovered a method whereby Compound I may be produced as the major product and as a significant major product.

The method of the present invention for producing Compound I as the major product comprises cultivating a particular mutant of *Zalerion arboricola* a identified as ATCC 20957 under aerobic conditions in a suitable medium containing assimilable sources of carbon, nitrogen and inorganic salts until a substantial amount of antifungal activity is produced as determined by assay against *Candida albicans* or by comparing with a previously prepared HPLC retention spectra as standard.

The mutant of *Z. arboricola* suitable for this process is produced by treating a spore suspension of *Z. arboricola* ATCC 20868 with a mutagen, plating the suspension onto a nutrient medium and incubating to develop colonies, isolating the colonies and preparing slant cultures. Although over a hundred different mutants were obtained by the procedure hereinafter described, only one mutant was found to accomplish the results achieved by the present invention. This culture which is identified in the Merck Culture Collection as MF 5404 has been deposited in the permanent culture collection of the American Type Culture Collection, 2301 Parklawn Drive, Rockville, Md. 20852 and is accessible under the accession number ATCC 20957.

The colonial and morphological description of ATCC 20957 are set forth below:

Colonies on potato-dextrose agar (Difco) at 20° C. slow-growing, attaining a diameter of 8–12 mm in one week. Mature colonies (3–4 weeks) on potato-dextrose agar effuse, with submerged and aerial hyphae, surface hairy, lanose, or funiculose, dull to moderately shiny, forming raised, densely compact colonies, with a substromatic texture due to dense conidia formation. Colony color pale olive-brown, olive, olive-brown, finally olive-black, Isabella Color, Sayal Brown, Tawny-olive, Saccardo's Umber, Sepia, Brownish Olive, Raw Umber, Dark Olive, Olivaceous Black (capitalized color names from R. Ridgway. 1912. Color Standards and Nomenclature, Washington, D.C.). Same colors in colony reverse. Odor, exudates, and soluble pigments absent.

Hyphae (in 3% KOH) pale yellow-brown to olive-brown, septate, branched, often with irregular lateral or terminal lobes, 1–3 um wide, thin- to slightly thick-walled, with walls smooth to slightly incrusted or verrucose. Aerial hyphae often adhering together in fascicles. Setae and hyphopodia absent.

Conidiogenous cells monoblastic, scattered to dense, integrated, terminal and intercalary, arising directly from undifferentiated hyphae, at right to slightly acute angles. Conidia originating as irregular chains, filaments, or coils, later developing as compact, irregular masses of 6–25 cells. Individual conidial cells, 3–6 um in diameter, globose, subglobose, or slightly irregular to lobed, smooth to finely verruculose, yellow-brown to olive brown.

For the production of the mutant, any of the agents commonly used to produce mutants may be employed. Thus, ultraviolet radiation, chemical mutagens, or intercalating agent may be employed. Suitable chemical mutagens include N-nitroso-N-methylurethane and N-methyl-N'-nitro-N-nitrosoguanidine.

The $Z.$ $arboricola$ mutant useful in the present invention was obtained by treating a spore suspension of $Z.$ $arboricola$ ATCC 20868 in 0.3M tris(hydroxymethyl)aminomethane (TRIS) buffer pH=7 with N-nitroso-N-methylurethane, plating the treated suspension on potato dextrose agar and incubating to develop colonies, thereafter isolating the colonies, transferring the separate colonies to slants of potato dextrose agar and incubating for 10 to 14 days at 25° C. to obtain cultures of mutants of $Z.$ $arboricola$, one of which was tentatively identified as Z7-9 and subsequently maintained as MF 5404 and deposited and assigned the accession number ATCC 20957.

The process of the present invention is carried out by cultivating $Z.$ $arboricola$ ATCC 20957 in a nutrient medium containing assimilable sources of carbon, nitrogen and inorganic salts until a substantial amount of Compound I has been produced.

Suitable sources of carbon include glycerol, sugars, sugar alcohols such as mannitol, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. One or several carbon sources may be employed in the same medium.

The sources of nitrogen include amino acids such as glycine, arginine, threonine, methionine and the like, ammonium salts, as well as complex sources such as yeast hydrolysates, yeast autolysates, yeast extracts, corn steep liquors, distillers solubles, cottonseed meal, meat extract, casein hydrolysates and the like. The various sources of nitrogen can be used alone or in combination in amounts ranging from 0.2 to 10 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

In producing the compounds, the culture is first grown in a seed medium and thereafter the culture is cultivated in a medium for production of the desired metabolite. A typical seed medium has the following composition:

| KF Seed Medium | per liter |
| --- | --- |
| Cerelose | 10 g |
| Corn steep liquor | 5 g |
| Tomato paste | 40 g |
| Oat flour | 10 g |
| Trace elements | 10 ml |

The trace element mixture is of the following composition:

|  | Per liter of 0.6N HCl |
| --- | --- |
| $FeSO_4.7H_2O$ | 1.0 g |
| $MnSO_4.4H_2O$ | 1.0 g |
| $CuCl_2.2H_2O$ | 0.025 g |
| $CaCl_2$ | 0.1 g |
| $H_3BO_3$ | 0.056 g |
| $(NH_4)_6Mo_7O_{24}.4H_2O$ | 0.01 g |
| $ZnSO.7H_2O$ | 0.2 g |

Although conventional nutrient production media may be employed, the use of certain nutrients such as mannitol and hydrolyzed casein or milk protein favors the production of the desired compound, and especially useful are the following media which have previously been described in application Ser. No. 374,416, filed Jun. 30, 1989, now abandoned, in a continuation-in-part application Ser. No. 07/492025 filed Mar. 12, 1990, now abandoned, and copending application Ser. No. 07/492026 filed Mar. 12,1990 now U.S. Pat. No. 5,021,341, the teachings of which are incorporated by reference. One of the media that is preferred is Medium I of the following composition:

| Medium I (S6) | Per liter |
| --- | --- |
| D-Mannitol | 44 g |
| $KH_2PO_4$ | 2 g |
| Glycine | 2 g |
| Peptonized Milk | 15 g |
| Lactic acid | 2 g |
| Trace elements | 10 ml |
| Soybean oil | 10 g |
| pre-sterilization pH 7.0 | |

Another especially useful medium is Medium II and is of the following composition:

| Medium II (TG 103) | Per liter |
| --- | --- |
| D-Mannitol | 40 g |
| NZ-Amine(type E)* | 33 g |
| Fidco-Yeast Extract | 10 g |
| (NH$_4$)$_2$SO$_4$ | 5 g |
| KH$_2$PO$_4$ | 9 g |
| no pH adjustment | |

*Casein hydrolysate, Humko-Sheffield, Memphis, Tenn.

Still another useful medium is Medium III of the following composition:

| Medium III (TG 102) | Per liter |
| --- | --- |
| D-Mannitol | 40 g |
| Bacto-Peptone | 33 g |
| Bacto-Yeast Extract | 10 g |
| (NH$_4$)$_2$SO$_4$ | 5 g |
| KH$_2$PO$_4$ | 9 g |
| no pH adjustment | |

The fermentation production medium inoculated with the culture growth is incubated for 3 to 30 days, usually 7 to 14 days, with or without agitation. The fermentation may be conducted aerobically at temperatures ranging from about 20° C. to about 40° C. For optimum results, it is most convenient to conduct these fermentations at a temperature in the range of from about 24° C. to about 30° C. Temperatures of about 24°–28° C. are most preferred. The pH of the nutrient medium suitable for producing the instant compounds can vary from about 5.0 to 8.5 with a preferred range of from about 5.5 to 7.5. After the appropriate period for the production of Compound I as determined by bioassay or HPLC against a previously established retention spectrum, Compound I may be harvested.

Compound I may be harvested from the fermentation medium by adding a water-immiscible organic solvent to the fermentation broth, separating and recovering the organic solution, vaporizing off the solvent to obtain Compound I as residue.

Alternatively, methanol may be added to the fermentation medium and after thorough mixing, filtered. The methanol solution may be evaporated to dryness to recover crude product residue, and the residue then dissolved in methanol for HPLC analysis and purification using silica gel chromatography with ester/alcohol mixtures with increasing concentration of alcohol for solution or preferably HPLC with C$_{18}$ reverse phase resin.

Isolation procedures for Compound I described in the aforementioned copending application, Ser. No. 374,416, the teachings of which are incorporated by reference, may be employed. However, with the elimination of a number of minor products in the process according to the present invention, the isolation procedure which employs chromatographic procedures is greatly simplified and the number of chromatographic separations necessary is greatly reduced.

Compound I has superior properties as a therapeutic agent in the treatment of mycotic infections against such species as *Candida albicans, Candida tropicalis* and *Candida parapsilosis* as well as in the treatment or prevention of *Pneumocystis carinii* infections. In such use Compound I is administered in a therapeutically effective or anti-infective amount to subjects infected with or to immune compromised subjects susceptible of being infected with Candida species or with *Pneumocystis carinii* as more fully disclosed in the aforecited copending application.

The following examples illustrate the invention but are not to be construed as limiting.

EXAMPLE I

A. Preparation of Mutant *Z. arboricola* ATCC 20957

A culture of *Z. arboricola* ATCC 20868 was grown on potato dextrose agar in petri plates at 25° C. for 3 weeks. Ten milliliters of 0.3M TRIS buffer, pH 7, were added to the plates and the spores scraped off the surface into the buffer with a sterile cotton swab. The suspension in the buffer was decanted off and the procedure repeated twice. The spore suspensions were combined and filtered through glass wool to remove large clusters of spores. The suspension filtrate was centrifuged at first at 600 rpm then at 700 rpm and finally at 800 rpm, each time for 3 minutes with the pellet being discarded after each centrifugation. The supernatant liquid from the third centrifugation was then centrifuged at 3000 rpm for 5 minutes. The pellet from this centrifugation was resuspended in 3 milliliters of 0.3M TRIS buffer and used for mutagenic treatment. This suspension contained from $10^3$ to $10^4$ spores per milliliter.

To the spore suspension was added 100 μg/ml of N-nitroso-N-methylurethane and the resulting mixture shaken at 300 rpm for 20 minutes at room temperature. At the end of this period, the mixture was centrifuged and the supernatant liquid was removed. The pellet was washed twice with 0.3M TRIS buffer pH 7.0 and then resuspended in the same buffer and after appropriate dilutions plated on potato dextrose agar for forming isolated colonies. The plates were incubated at 25° C. for two weeks for colony formation. The colonies were isolated by separately transferring to slants of potato dextrose agar. The inoculated slants were incubated at 25° C. for 10–14 days and a plug from the slants taken and tested for the production of Compounds I and X and other components in the fermentation by HPLC assay. A plug from one of the slants initially designated as Z7-9, which subsequently was placed in the Merck Culture Collection as MF 5404 and deposited with the American Type Culture Collection as ATCC 20957, was employed in the following fermentation.

B. Production of Compound I Fermentation and Harvest

Seed cultures were first prepared by inoculating twenty milliliters of KF seed medium (previously defined) in an unbaffled Erlenmeyer flask with a plug from the slant identified as Z7-9. The flasks were shaken at 220 rpm and 25° C. for 96 hours to produce a seed culture.

Forty milliliters of Medium I (S6) in 250 milliliters of unbaffled Erlenmeyer flask was inoculated with 2 milliliters of the seed developed as described above. The inoculated flasks were shaken at 220 rpm and 25° C. for 14 days and the contents then analyzed for the production of the secondary metabolites by HPLC assay.

After completion of the cultivation the broth was homogenized and to twenty milliliters of it was added an equal volume of methyl ethyl ketone and the mixture shaken for 30 minutes on a reciprocating shaker. The organic and aqueous phases were separated by centrifugation at 3000 rpm and the methyl ethyl ketone layer evaporated to dryness in vacuo to obtain a residue. The latter was dissolved in 1 milliliter of methanol and centrifuged for 5 minutes. The resulting clarified solution was diluted with methanol and recentrifuged. The supernatant was then subjected to an HPLC analysis carried out using the following conditions:

Column: Whatman Partisil C18 ODS-3,5 μm, 25 cm
   Solvent: Water/Acetonitrile, 54/46
   Flow rate: 0.75 ml/min
   Column temperature: 40° C.
   Detection: 210 nm The fractions were collected with a commercial fraction collector, fitted with 96 well, flat bottom, microtiter plates at a rate of one fraction per 0.3 minute. After completion of the collection, the HPLC solvent was evaporated in a high speed vacuum concentrator. Then to each well was added 0.2 milliliter of potato dextrose broth which previously had been inoculated with *Candida albicans* MY 1028 and grown for 24 hours. The volume of the inoculum was 0.2 milliliter per 100 milliliters of medium. The plates were then incubated overnight and observed for growth. The fractions which were bioactive inhibited the growth of *C. albicans* MY 1028.

Similarly, seed cultures were prepared by inoculating a plug from MF 5171 into KF seed medium and the inoculated medium shaken at 220 rpm and 25° C. for 96 hours to produce a seed culture. Forty milliliters of Medium I (S6) in 250 milliliters of unbaffled Erlenmeyer flask was inoculated with 2 milliliters of the seed culture. The inoculated flasks were shaken at 220 rpm and 25° C. for 14 days and the contents analyzed for the production of the secondary metabolites by the HPLC assay. The broth then was extracted with methyl ethyl ketone and the organic layer evaporated to dryness to recover the metabolite as residue. The residue was dissolved in methanol and subjected to HPLC as above described and the fractions collected in the microtiter plate fraction collector. The wells then were filled with potato dextrose broth which previously had been inoculated with *C. albicans* MY 1028, and the plate incubated and observed for growth.

The bioactive fractions were correlated with relative retention time determined for the various components produced during cultivation of *Z. arboricola* MF 5171 (ATCC 20868). The results of the amounts of compounds produced as determined from HPLC chromatogram and compared with a previously prepared reference standard were as follows:

| Culture | Compound I | Compound X |
|---|---|---|
| | μg/l | |
| MF 5171 (parent) | 18 | 75 |
| MF 5464 (mutant) | 35 | 12 |

EXAMPLE II 250 milliliter flasks were prepared containing 54 milliliters of KF seed medium (similar to that previously given except that 10 grams of cerelose was replaced with 10 grams of glucose).

The flasks were inoculated from an agar slant MF 5404 of *Zalerion arboricola* ATCC 20957 and incubated at 25° C. for four days at 220 rpm. A 20 ml sample was used to inoculate each of four 2 liter flasks containing 500 ml of KF medium. The flasks were incubated at 25° C. for three days at 220 rpm. The flask contents were then pooled for use as inoculum for a 300 liter seed fermenter containing 180 liters of KF medium and 2 ml/liter polypropylene glycol P-2000 (Dow Chemical Co.) added to reduce foaming. The seed fermenter was operated for three days at a temperature of 25° C., an air flow of 90 liters/min, a pressure of 0.7 kg/cm$^2$ gauge, and an agitator speed of 200 rpm. A 25 liter sample was used to inoculate an 800 liter production fermenter containing 475 liters of Medium II (TG103) of the composition previously given but to which 2 ml/liter of polypropylene glycol P-2000 had been added and sterilized at 120° for 25 minutes. The fermentation was carried out for five days at a temperature of 25° C., an air flow of 250 liters/minute, a pressure of 0.7 kg/cm$^2$ gauge, and an agitator speed of 150 rpm. The pH was allowed to decrease from an initial value of 6.0 to 5.5, and then maintained at 5.5±0.4 using NaOH and H$_2$SO$_4$. After five days the broth from two batches was harvested for product isolation.

Seven hundred and fifty liters of methanol was added to 750 liters of fermentation whole broth and the mixture agitated for 8 hours. The whole broth extract was centrifuged to remove the insoluble fermentation solids and to yield 1436 liters of clarified supernatant, which was adjusted to pH 7.

A 77 liter "Diaion" SP-207 (Mitsubishi Chemical Industries) bed was prepared by washing with methanol and pre-equilibrating with 50:50 methanol/water (MeOH/H$_2$O). The clarified supernatant was then charged to the SP-207 in an upflow direction at a fluidized bed rate of 5.7 liters per minute. After charging, the column was washed with 567 liters of 65:35 methanol water and eluted with 454 liters 100% methanol.

The 65:35 MeOH/H$_2$O and 100% MeOH SP-207 cuts from the SP-207 column were combined and adjusted to a composition 50:50 of MeOH/H$_2$O by the addition of water to yield a 945 liter rich cut. This rich cut was charged to a 108 liter "Diaion" HP-20 column (washed with methanol and pre-equilibrated with MeOH/H$_2$O 50:50) at a flow rate of 2–4 liters per minute. The resin was then washed with 567 liters MeOH/H$_2$O 65:35 and eluted with 454 liters 100% MeOH.

The HP-20 cut rich in Compound I was concentrated to a volume of 6 liters, by first diluting with water and then adsorbing and eluting from smaller HP-20 column (10 liters) in a manner similar to that employed in the larger HP-20 column.

Two liters (of a total of 6 liters) of the concentrated HP-20 rich cut was diluted with 2 liters of water and charged to a 800 A Preparative HPLC system (of Separations Technology) equipped with a 3.9 liter C18 column (Amicon) pre-washed with MeOH and preequilibrated with MeOH/H$_2$O 50:50. The charge was followed by 500 ml of MeOH/H$_2$O 50:50 and eluted at a flow rate of 212 ml/min with a linear gradient from MeOH/H$_2$O 50:50 to 100 percent MeOH in a 60 minute time period. Fractions were analyzed via HPLC, combined and concentrated to dryness to yield approximately 20 grams Compound I of 88 percent purity.

Compound I is an antibiotic agent useful for the control of fungi, especially those causing mycotic infections such as the Candida species and also for the control of *Pneumocystis carinii*, an organism especially troublesome to immune compromised patients such as those under chemotherapeutic treatments or AIDS patients. The utility of Compound I is more fully disclosed and described in the aforecited copending application Ser. No. 374,416.

What is claimed is:

1. A method for producing a compound of the formula

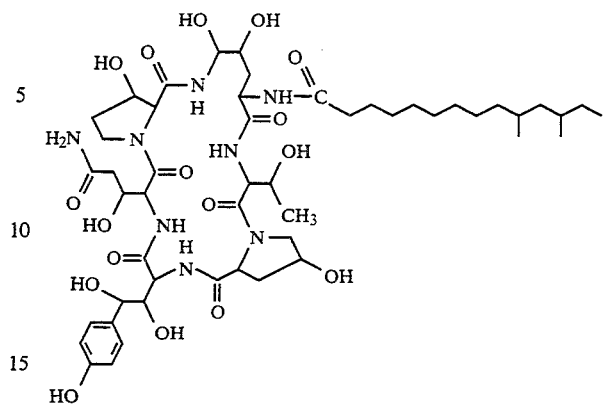

as the predominant antibiotic product comprising cultivating *Zalerion arboricola* MF-504, ATCC 20957 under aerobic conditions in a nutrient medium containing assimilable sources of carbon, nitrogen and inorganic salts, which medium includes mannitol and either hydrolyzed casein or other hydrolyzed milk proteins as nutrients, continuing the cultivation until the production of said compound of formula (I) is complete as determined by bioassay or HPLC assay, and thereafter separating said compound from the medium.

* * * * *

UNITED STATES PATENT AND TRADEMARK OFFICE
CERTIFICATE OF CORRECTION

PATENT NO.   : 5,426,038
DATED        : JUN. 20, 1995
INVENTOR(S)  : Jimmy M. Fountoulakis, Prakash S. Masurekar, Louis Kaplan It is certified that error appears in the above-indentified patent and that said Letters Patent is hereby corrected as shown below:

Claim 1, Column 10, line 19, change "MF-504" to -- MF-5404 --.

Signed and Sealed this

Third Day of October, 1995

Attest:

BRUCE LEHMAN

*Attesting Officer*        *Commissioner of Patents and Trademarks*